United States Patent

Henning et al.

[11] Patent Number: 5,204,357
[45] Date of Patent: Apr. 20, 1993

[54] RENIN-INHIBITING AMINO ACID DERIVATIVES

[75] Inventors: Rainer Henning, Hattersheim am Main; Hansjörg Urbach; Dieter Ruppert, both of Kronberg/Taunus; Bernward Schölkens, Kelkheim (Taunus), all of Fed. Rep. of Germany

[73] Assignee: Hoechst Aktiengesellschaft, Frankfurt am Main, Fed. Rep. of Germany

[21] Appl. No.: 310,183

[22] Filed: Feb. 14, 1989

[30] Foreign Application Priority Data

Feb. 16, 1988 [DE] Fed. Rep. of Germany ....... 3804793

[51] Int. Cl.$^5$ .................. A61K 31/44; A61K 31/47; C07D 401/04; C07D 401/06; C07D 211/82; C07D 211/84; C07D 211/86

[52] U.S. Cl. .................. 514/307; 514/332; 514/333; 514/334; 514/335; 514/337; 514/338; 514/340; 514/342; 514/343; 514/346; 514/347; 514/348; 514/349; 514/350; 514/351; 514/352; 514/354; 514/355; 514/356; 514/357; 546/146; 546/147; 546/256; 546/257; 546/258; 546/261; 546/270; 546/274; 546/278; 546/291; 546/292; 546/293; 546/294; 546/296; 546/297; 546/298; 546/299; 546/300; 546/304; 546/307; 546/308; 546/309; 546/310; 546/311; 546/312; 546/330; 546/331; 546/334; 546/335; 546/336; 546/337

[58] Field of Search .............. 546/278, 270, 274, 330, 546/331, 334, 335, 336, 337, 146, 147, 256, 257, 258, 261, 291, 292, 293, 294, 296, 297, 298, 299, 300, 304, 307, 308, 309, 310, 311, 312; 514/341, 307, 337, 338, 340, 343, 342, 357, 332, 333, 334, 335, 346, 347, 348, 349, 350, 351, 352, 354, 355, 356

[56] References Cited

FOREIGN PATENT DOCUMENTS 6859587 2/1987 Australia .
0236734 9/1987 European Pat. Off. .
870868 2/1987 South Africa .

OTHER PUBLICATIONS

Burger, A. Medicinal Chemistry, 2nd Ed. pp. 565–601 (1960).
Haber et al.; J. of Cardiovascular Pharm. pp. 554–558 (1987).
Denkewalter et al. Progress in Drug. Research, pp. 510–512 (1966).
Bolis et al. Renin Inhibitors, J. Medicinal Chemistry, vol. 30, No. 10, pp. 1729–1737 (1987).
Plattner et al.; J. Medicinal Chem. vol. 31, No. 12, pp. 2277–2288 (1988).
Browne et al. Chem. Abstracts vol. 111; 58354v (1989).

Primary Examiner—Johann Richter
Attorney, Agent, or Firm—Finnegan, Henderson, Farabow, Garrett & Dunner

[57] ABSTRACT

The invention relates to compounds of the formula I $$A-B-NH-\underset{|}{\overset{R^1}{C}H}-\underset{|}{\overset{R^2}{C}H}-\underset{|}{\overset{}{C}H}-R^3,$$
$$\phantom{A-B-NH-CH-CH-}OR^9$$

(I)

in which A represents a substituted thio-, sulfinyl- or sulfonyl-alkanoyl radical or a four- to eleven-membered heterocycle, B is an amino acid residue, $R^1$ denotes hydrogen (substituted) alkyl, (substituted)cycloalkyl or aryl, $R^2$ represents hydrogen, (substituted)alkyl or aryl, $R^3$ denotes a radical of the formula —$(CH_2)_q$—(X-)$_r$—$(CH_2)_s$—$R^6$ with X denoting $CF_2$, CO or $CHR^8$, $R^6$ denoting a (substituted)heteroaromatic, $R^8$ denoting alkyl, alkoxy, alkylthio, alkylamino, hydroxyl, azide or halogen, q and s denoting 1 to 4, and r denoting 0 or 1, and $R^9$ is hydrogen, (substituted)alkyl, alkanoyl, cycloalkanoyl, (substituted) aroyl or (substituted)aryl, and to the salts thereof. In addition, processes for the preparation of these compounds, and the use thereof as renin inhibitors are described.

7 Claims, No Drawings

RENIN-INHIBITING AMINO ACID DERIVATIVES

DESCRIPTION

The invention relates to amino acid derivatives which inhibit the action of the natural enzyme renin, and to a process for the preparation thereof and the use thereof.

European Patent Application No. 236 734 discloses 5-amino-4-hydroxyvaleryl derivatives which are substituted by sulfur-containing groups and have a renin-inhibiting action.

It has now been found, surprisingly, that compounds which differ from the compounds described in EP-A 236 734 especially in the structure of the C-terminal building blocks are highly effective renin inhibitors both in vitro and in vivo.

The invention relates to compounds of the formula I

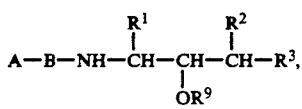

in which
A denotes a radical of the formula II

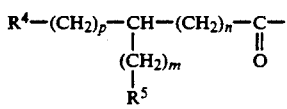

in which
$R^4$
a) represents a radical of the formula IV $$R^7-S(O)_t-\qquad (IV)$$

with
$R^7$ being $(C_1-C_{10})$-alkyl which can be substituted by one or more functional groups, for example oxo, hydroxyl, etherified hydroxyl, for example $(C_1-C_6)$-alkoxy such as methoxy or ethoxy, or phenyloxy; esterified hydroxyl, for example $(C_1-C_6)$-alkanoyloxy such as acetoxy; halogen, for example chlorine or bromine; hydroxysulfonyloxy; carboxyl; esterified carboxyl, for example $(C_1-C_4)$-alkoxycarbonyl such as methoxy- or ethoxycarbonyl; amidated carboxyl, for example carbamoyl or mono- or di-$(C_1-C_4)$-alkylcarbamoyl such as methyl- or diemthylcarbamoyl; cyano; amino; substituted amino, for example mono-$(C_1-C_4)$-alkylamino or di-$(C_1-C_4)$-alkylamino; acylamino or substituted amino in which the amino group is part of a five- or six-membered heterocycle containing one or two nitrogen atoms and, if desired, one oxygen or sulfur atom; $(C_2-C_8)$-alkenyl, $(C_2-C_8)$-alkynyl, both of which can be substituted as alkyl; hydroxyl; $(C_1-C_6)$-alkoxy; $(C_3-C_8)$-cycloalkyl; $(C_5-C_{10})$-bicycloalkyl; $(C_8-C_{10})$-tricycloalkyl; $(C_3-C_8)$-cycloalkyl-$(C_1-C_{10})$-alkyl; $(C_6-C_{14})$-aryl, $(C_6-C_{14})$-aryloxy, $(C_6-C_{14})$-aryl-$(C_1-C_{10})$-alkyl, which are substituted in the aryl moiety optionally by one or two identical or different radicals from the group comprising F, Cl, Br, hydroxyl, $(C_1-C_7)$-alkoxy, $(C_1-C_7)$-alkyl, $(C_1-C_7)$-alkoxycarbonyl, amino or trifluoromethyl; a saturated, aromatic or partially aromatic heterocycle which can be mono-, bi- or tricyclic and contains at least one carbon atom, one to four nitrogen atoms and/or one sulfur or oxygen atom as ring members and is substituted by one, two or three, preferably one or two, identical or different radicals from the group comprising F, Cl, Br, hydroxyl, $(C_1-C_7)$-alkoxy, $(C_1-C_7)$-alkyl, $(C_1-C_7)$-alkoxycarbonyl, amino, phenyl or trifluoromethyl; amino, substituted amino, for example mono-$(C_1-C_4)$-alkylamino, di-$(C_1-C_4)$-alkylamino, acylamino or substituted amino in which the amino group is part of a five- or six-membered heterocycle containing one or two nitrogen atoms and, if desired, one oxygen or sulfur atom, or can be substituted by oxo; and t is 0, 1 or 2; or b) denotes a saturated or partially unsaturated four-to ten-membered monocyclic or seven- to eleven-membered bicyclic heterocycle having in each case one sulfur atom or an SO or $SO_2$ group, each of which can be substituted by one or two $(C_1-C_6)$-alkyl, $(C_6-C_{14})$-aryl or $(C_6-C_{14})$-aryl-$(C_1-C_6)$-alkyl radicals, it being possible for each aryl moiety to be optionally substituted as described under a);

$R^5$ denotes phenyl, 2- or 3-thienyl, 2-, 3- or 4-pyridyl, 1-, 2- or 4-imidazolyl, 1- or 2-naphthyl or 2- or 3-benzo[b]thienyl, each of which is optionally substituted by one, two or three radicals from the group comprising hydroxyl, $(C_1-C_4)$-alkyl, $(C_1-C_4)$-alkoxy, Cl, F, Br, nitro, amino, acetamido, trifluoromethyl or one methylenedioxy radical;

m denotes 0, 1, 2 or 3;
n denotes 0, 1 or 2;
p denotes 0, 1 or 2;

B denotes a residue, which is linked N-terminal to A and C-terminal to

of an amino acid from the group comprising phenylalanine, histidine, tyrosine, tryptophan, methionine, leucine, isoleucine, asparagine, aspartic acid, β-2-thienylalanine, β-3-thienylalanine, β-2-furylalanine, β-3-furylalanine, lysine, ornithine, valine, alanine, 2,4-diaminobutyric acid, arginine, 4-chlorophenylalanine, methionine sulfone, methionine sulfoxide, 2-pyridylalanine, 3-pyridylalanine, cyclohexylalanine, cyclohexylglycine, immethylhistidine, O-methyltyrosine, O-benzyltyrosine, O-tert.-butyltyrosine, phenylglycine, 1-naphthylalanine, 2-naphthylalanine, 4-nitrophenylalanine, norvaline, β-2-benzo[b]thienylalanine, β-3-benzo[b]thienylalanine, 2-fluorophenylalanine, 3-fluorophenylalanine, 4-fluorophenylalanine, norleucine, cysteine, S-methylcysteine, 1,2,3,4-tetrahydroisoquinoline-3-carboxylic acid, homophenylalanine, DOPA, O-dimethyl-DOPA, 2-amino-4-(2-thienyl)butyric acid, benzodioxol-5-ylalanine, N-methylhistidine, 2-amino-4-(3-thienyl)-butyric acid, 3-(2-thienyl)serine, (Z)-dehydrophenylalanine, (E)-dehydrophenylalanine, 1,3-dioxolan-2-ylalanine, N-pyrrolylalanine, 1-, 3- or 4-pyrazolylalanine;

$R^1$ denotes hydrogen, $(C_1-C_{10})$-alkyl, $(C_4-C_7)$-cycloalkyl, $(C_4-C_7)$-cycloalkyl-$(C_1-C_4)$-alkyl, $(C_6-C_{14})$-aryl, $(C_6-C_{14})$-aryl-$(C_1-C_4)$-alkyl or 1,3-dithiolan-2-yl-$(C_1-C_4)$-alkyl;

$R^2$ denotes hydrogen, $(C_1-C_{10})$-alkyl, $(C_6-C_{14})$-aryl or $(C_6-C_{14})$-aryl-$(C_1-C_4)$-alkyl;

$R^3$ denotes a radical of the formula III $$-(CH_2)_q-(X)_r-(CH_2)_s-R^6 \quad \text{(III)}$$

in which $R^6$ represents hydrogen, hydroxyl, amino or a five- or six-membered monocyclic or nine- or ten-membered bicyclic heteroaromatic having at least one carbon atom, one to four nitrogen atoms and/or one sulfur or oxygen atom as ring members;

X denotes $-CF_2-$, $-CO-$ or $-CHR^8-$, where $R^8$ represents $(C_1-C_7)$-alkyl, $(C_1-C_5)$-alkoxy, $(C_1-C_5)$-alkylthio, $(C_1-C_5)$-alkylamino, $-OH$, $-N_3$, $-F$, $-Cl$, $-Br$ or $-I$;

q and s denote, independently of one another, 0, 1, 2, 3 or 4; and r denotes 0 or 1, with the proviso that if $R^4$ represents a radical of the formula $R^7-S(O)_t-$ (IV) with t=2, r is 0 or n is not 0 (formula II); and $R^9$ denotes hydrogen; $(C_1-C_{10})$-alkyl; $(C_1-C_6)$-alkanoyl; $(C_6-C_9)$-cycloalkanoyl; phenyl, phenyl-$(C_1-C_4)$-alkyl or benzoyl, each of which is optionally substituted in the aromatic by one, two or three radicals from the group comprising $(C_1-C_4)$-alkyl, $(C_1-C_4)$-alkoxy, Cl, F, Br, nitro, trifluoromethyl or one methylenedioxy; $(C_1-C_6)$-alkanoyloxy-$(C_1-C_2)$-alkyl, $(C_1-C_6)$-alkoxycarbonyloxy-$(C_1-C_2)$-alkyl or

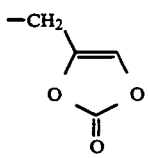

as well as the physiologically tolerated salts thereof.

The chirality centers in the compounds of the formula I can have the R or S or R,S configuration.

Alkyl can be straight-chain or branched. A corresponding statement applies to radicals derived therefrom, such as, for example, alkoxy, alkylthio, alkylamino, dialkylamino, alkanoyl and aralkyl.

Cycloalkyl is to be understood to include alkyl-substituted radicals such as, for example, 4-methylcyclohexyl or 2,3-dimethylcyclopentyl.

Examples of $(C_6-C_{14})$-aryl are phenyl, naphthyl, biphenylyl or fluorenyl; phenyl is preferred. Corresponding statements apply to radicals derived therefrom, such as, for example, aryloxy, aroyl, aralkyl and aralkyloxy. Aralkyl is to be understood to be unsubstituted or substituted $(C_6-C_{14})$-aryl radical which is linked to $(C_1-C_6)$-alkyl, such as, for example, benzyl, α- and β-naphthylmethyl, halobenzyl and alkoxybenzyl, but with aralkyl not being restricted to the radicals mentioned.

Examples of bicycloalkyl are bicyclohexyl, -heptyl, -octyl, -nonyl or -decyl, for example bicyclo[3.1.0]hex-1-, -2- or -3-yl, bicyclo[4.1.0]hept-1- or -7-yl, bicyclo[2.2.1]hept-2-yl, for example endo- or exo-norbornyl, bicyclo[3.2.1]oct-2-yl, bicyclo[3.3.0]oct-3-yl or bicyclo[3.3.1]non-9-yl, as well as α- or β-decahydronaphthyl.

Tricycloalkyl contains, for example, 8 to 10 carbon atoms and is, for example, tricyclo[5.2.1.0$^{2,6}$]dec-8-yl or adamantyl, such as 1-adamantyl. Examples of a five- or six-membered monocyclic or nine- or ten-membered bicyclic heteroaromatic having at least one carbon atom, one to four nitrogen atoms and/or one sulfur or oxygen atom as ring members are pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl or a benzo-fused or cyclopenta-, cyclohexa- or cyclohepta-fused derivative of these radicals. This heterocycle can be substituted on one nitrogen atom by oxide, $(C_1-C_6)$-alkyl, for example methyl or ethyl, phenyl or phenyl-$(C_1-C_4)$-alkyl, for example benzyl, and/or on one or more carbon atoms by $(C_1-C_4)$-alkyl, for example methyl, phenyl, phenyl-$(C_1-C_4)$-alkyl, for example benzyl, halogen, for example chlorine, hydroxyl, $(C_1-C_4)$-alkoxy, for example methoxy, phenyl-$(C_1-C_4)$-alkoxy, for example benzyloxy, or oxo, and can be partially saturated, and examples are 2- or 3-pyrrolyl, phenylpyrrolyl, for example 4- or 5-phenyl-2-pyrrolyl, 2-furyl, 2-thienyl, 4-imidazolyl, methylimidazolyl, for example 1-methyl-2-, -4- or -5-imidazolyl, 1,3-thiazol-2-yl, 2-, 3- or 4-pyridyl, 2-, 3- or 4-pyridyl 1-oxide, 2-pyrazinyl, 2-, 4- or 5-pyrimidinyl, 2-, 3- or 5-indolyl, substituted 2-indolyl, for example 1-methyl-, 5-methyl-, 5-methoxy-, 5-benzyloxy-, 5-chloro- or 4,5-dimethyl-2-indolyl, 1-benzyl-2- or -3-indolyl, 4,5,6,7-tetrahydro-2-indolyl, cyclohepta[b]-5-pyrrolyl, 2-, 3- or 4-quinolyl, 4-hydroxy-2-quinolyl, 1-, 3- or 4-isoquinolyl, 1-oxo-1,2-dihydro-3-isoquinolyl, 2-quinoxalinyl, 2-benzofuranyl, 2-benzoxazolyl, 2-benzothiazolyl, benzo[e]indol-2-yl or β-carbolin-3-yl.

Alkanoyloxyalkyl is to be understood to be, for example, acetoxymethyl, acetoxyethyl, pivaloyloxymethyl, pivaloyloxyethyl or 2,2-dimethylbutyryloxymethyl, and alkoxycarbonyloxyalkyl is to be understood to be, for example, ethoxycarbonyloxymethyl, ethoxycarbonyloxyethyl, tert.-butoxycarbonyloxymethyl and tert.-butoxycarbonyloxyethyl.

Examples of suitable S-, SO- or $SO_2$-containing heterocycles for $R^4$ are: dihydrothiophene, tetrahydrothiophene, thiopyran, dihydrothiopyran, tetrahydrothiopyran, hexahydrothiepine, octahydrothiocine, octahydrocyclopenta[b]thiophene, octahydrocyclopenta[c]thiophene, dihydrobenzothiophene, octahydrobenzothiophene, octahydroisobenzothiophene, dihydroisobenzothiophene, decahydrocyclohepta[b]thiophene, decahydrocyclohepta[c]thiophene and their SO and $SO_2$ analogs.

Salts of compounds of the formula I are to be understood to be, in particular, pharmaceutically utilizable or non-toxic salts.

Salts of this type are formed, for example by compounds of the formula I which contain acidic groups, for example carboxyl, with alkali metals or alkaline earth metals such as Na, K, Mg and Ca, as well as with physiologically tolerated organic amines such as, for example, triethylamine and tri-(2-hydroxyethyl)amine.

Compounds of the formula I which contain basic groups, for example an amino group or a guanidino group, form salts with inorganic acids such as, for example, hydrochloric acid, sulfuric acid or phosphoric acid and with organic carboxylic or sulfonic acids such as, for example, acetic acid, citric acid, benzoic acid, maleic acid, fumaric acid, tartaric acid and p-toluenesulfonic acid.

Preferred compounds of the formula I are those in which A denotes a radical of the formula II in which $R^4$ a) represents a radical of the formula IV with $R^7$ methyl, ethyl, isopropyl, tert.-butyl, 2-hydroxyethyl, 2-methoxyethyl, 2-phenoxyethyl, 2-acetoxyethyl, carboxymethyl, 2-carboxyethyl, methoxycarbonylmethyl, 2-methoxycarbonylethyl, ethoxycarbonylmethyl, 2-ethoxycarbonylethyl, carbamoylmethyl, 2-carbamoylethyl, 2-aminoethyl, 2-dimethylaminoethyl, 2-morpholinoethyl, 2-piperidinoethyl, 2-benzyloxycarbonylaminoethyl, 2-tert.-butoxycarbonylaminoethyl, 2-oxopropyl or 2-oxobutyl, vinyl, allyl or 2- or 3-butenyl, ethinyl, 1-propinyl, or 2-propinyl, cyclopropyl, cyclobutyl, cyclopentyl or cyclohexyl, bicyclo-[2.2.1]hept-2-yl, 1-adamantyl, cyclopropylmethyl, cyclobutylmethyl, cyclopentylmethyl or cyclohexylmethyl, phenyl, 1- or 2-naphthyl, o-, m- or p-methylphenyl, o-, m- or p-hydroxyphenyl or o-, m- or p-aminophenyl, benzyl, 2-phenylethyl or α- or β-naphthylmethyl, unsubstituted or substituted heteroaryl, for example 2- or 3-pyrrolyl, 2-furyl, 2-thienyl, 2- or 4-imidazolyl, 1-methyl-2-, -4- or -5-imidazolyl, 1,3-thiazol-2-yl, 2-, 3- or 4-pyridyl, 2-, 3- or 4-pyridyl 1-oxide, 2-pyrazinyl, 2-, 4- or 5-pyrimidinyl, 2-, 3- or 4-quinolyl, 1-, 3- or 4-isoquinolyl or 2-benzoxazolyl, hydroxyl, substituted hydroxyl, for example methoxy, ethoxy or n-butoxy, or aryloxy, for example phenoxy, 4-hydroxyphenoxy or 3,4-methylenedioxyphenoxy, amino or substituted amino, for example methylamino, ethylamino, isopropylamino, n- or tert.-butylamino, dimethylamino or diethylamino, or amino as part of a five- or six-membered ring containing one nitrogen atom and, if desired, one oxygen atom, for example 1-pyrrolidinyl, 1-piperidinyl or 4-morpholinyl; and t 0, 1 or 2; or b) denotes a saturated or partially unsaturated four- to seven-membered monocyclic or seven- to ten-membered bicyclic heterocycle, each having one sulfur atom or an SO or $SO_2$ group, it being possible for the monocyclic heterocycle to be substituted by one or two ($C_1$-$C_4$)-alkyl or phenyl radicals;

$R^5$ denotes phenyl, 2-thienyl, 2-pyridyl, 1-naphthyl, 2-benzo[b]thienyl or 3-benzo[b]thienyl, each of which is optionally substituted by one, two or three radicals from the group comprising methyl, ethyl, isopropyl, tert.-butyl, methoxy, hydroxyl, F, Cl, nitro, trifluoromethyl or one methylenedioxy radical;

m is 0, 1 or 2;

n is 0 or 1;

p denotes 0 or 1;

B represents a bivalent residue from the group comprising phenylalanine, histidine, tyrosine, tryptophan, methionine, leucine, isoleucine, asparagine, aspartic acid, β-2-thienylalanine, β-3-thienylalanine, β-2-furylalanine, lysine, ornithine, 2,4-diaminobutyric acid, arginine, norvaline, 4-chlorophenylalanine, methionine sulfone, methionine sulfoxide, 2-pyridylalanine, 3-pyridylalanine, cyclohexylalanine, cyclohexylglycine, im-methylhistidine, O-methyltyrosine, O-benzyltyrosine, O-tert.-butyltyrosine, phenylglycine, 1-naphthylalanine, 2-naphthylalanine, 4-nitrophenylalanine, norleucine, valine, alanine, cysteine, S-methylcysteine, N-methylhistidine, benzodioxol-5-ylalanine, 1,2,3,4-tetrahydroisoquinoline-3-carboxylic acid, homophenylalanine, 2-amino-4-(2-thienyl)butyric acid, (Z)-dehydrophenylalanine, (E)-dihydrophenylalanine or 1,3-dioxolan-2-ylalanine;

$R^1$ denotes isobutyl, benzyl or cyclohexylmethyl;

$R^2$ is hydrogen, methyl, isopropyl or isobutyl;

$R^3$ represents a radical of the formula III in which $R^6$ denotes hydrogen, hydroxyl, amino or a five- or six-membered monocyclic or nine- or ten-membered bicyclic heteroaromatic having at least one carbon atom, one to four nitrogen atoms and/or one sulfur or oxygen atom as ring members;

X is —$CF_2$—, —CO— or —$CHR^8$—, where $R^8$ denotes ($C_1$-$C_4$)-alkyl, for example methyl, ethyl, n-propyl or isopropyl, ($C_1$-$C_4$)-alkoxy, for example methoxy, ethoxy, n-propoxy or isopropoxy, —OH, —$N_3$, —F or —Cl;

q and s are, independently of one another, 0, 1, 2 or 3;

r is 0 or 1, with the proviso that if $R^4$ represents a radical of the formula IV with t=0, r is 0 or n is not 0 (formula II); and $R^9$ denotes hydrogen, acetoxymethyl, acetoxyethyl, pivaloyloxymethyl, pivaloyloxyethyl, 2,2-dimethylbutyryloxymethyl, ethoxycarbonyloxymethyl, ethoxycarbonyloxyethyl, tert.-butoxycarbonyloxymethyl or tert.-butoxycarbonyloxyethyl;

as well as the physiologically tolerated salts thereof.

Particularly preferred compounds of the formula I are those in which

A represents a radical of the formula II in which $R^4$ a) denotes a radical of the formula IV with $R^7$ methyl, ethyl, isopropyl, tert.-butyl, 2-hydroxyethyl, 2-methoxyethyl, 2-phenoxyethyl, 2-acetoxyethyl, carboxymethyl, 2-carboxyethyl, methoxycarbonylmethyl, 2-methoxycarbonylethyl, ethoxycarbonylmethyl, 2-ethoxycarbonylethyl, carbamoylmethyl, 2-carbamoylethyl, 2-aminoethyl, 2-dimethylaminoethyl, 2-morpholinoethyl, 2-piperidinoethyl, 2-benzyloxycarbonylaminoethyl, 2-tert.-butoxycarbonylaminoethyl, 2-oxopropyl or 2-oxobutyl, vinyl, allyl or 2- or 3-butenyl, ethinyl, 1-propinyl, or 2-propinyl, cyclopropyl, cyclobutyl, cyclopentyl or cyclohexyl, bicyclo[2.2.1]hept-2-yl, 1-adamantyl, cyclopropylmethyl, cyclobutylmethyl, cyclopentylmethyl or cyclohexylmethyl, phenyl, 1-or 2-naphthyl, o-, m- or p-methylphenyl, o-, m- or p-hydroxyphenyl or o-, m- or p-aminophenyl, benzyl, 2-phenylethyl or α- or β-naphthylmethyl, unsubstituted or substituted heteroaryl, for example 2- or 3-pyrrolyl, 2-furyl, 2-thienyl, 2- or 4-imidazolyl, 1-methyl-2-, -4- or -5-imidazolyl, 1,3-thiazol-2-yl, 2-, 3- or 4-pyridyl, 2-, 3- or 4-pyridyl 1-oxide, 2-pyrazinyl, 2-, 4- or 5-pyrimidinyl, 2-, 3-or 4-quinolyl, 1-, 3- or 4-isoquinolyl or 2-benzoxazolyl, hydroxyl, substituted hydroxyl, for example methoxy, ethoxy or n-butoxy, or aryloxy, for example phenoxy, 4-hydroxyphenoxy or 3,4-methylenedioxyphenoxy, amino or substituted amino, for example methylamino, ethylamino, isopropylamino, n- or tert.-butylamino, dimethylamino or diethylamino, or amino as part of a five- or six-membered ring containing one nitrogen atom and, if desired, one oxygen atom, for example 1-pyrrolidinyl, 1-piperidinyl or 4-morpholinyl; and t 0, 1 or 2; or b) represents dioxides of tetrahydrothiophene, tetrahydrothiopyran, hexahydrothiepine, octahydrocyclopenta[b]thiophene, octahydrocyclopenta[c]thiophene, octahydrobenzothiophene or octahydroisobenzothiophene;

$R^5$ denotes phenyl, 2-thienyl, 2-pyridyl, 1-naphthyl, each of which is optionally substituted by hydroxyl, dihydroxy, methoxy, dimethoxy, ethoxy, isopropoxy, F, Cl or methylenedioxy;

m is 1 or 2;

n denotes 0 and p denotes 0 or 1,

B represents a bivalent residue from the group comprising phenylalanine, histidine, tyrosine, tryptophan, methionine, leucine, isoleucine, asparagine, aspartic acid, β-2-thienylalanine, β-3-thienylalanine, β-2-furylalanine, lysine, ornithine, 2,4-diaminobutyric acid, arginine, norvaline, 4-chlorophenylalanine, methionine sulfone, methionine sulfoxide, 2-pyridylalanine, 3-pyridylalanine, cyclohexylalanine, cyclohexylglycine, im-methylhistidine, O-methyltyrosine, O-benzyltyrosine, O-tert.-butyltyrosine, phenylglycine, 1-naphthylalanine, 2-naphthylalanine, 4-nitrophenylalanine, norleucine, valine, alanine, cysteine, S-methylcysteine, N-methylhistidine, benzodioxol-5-ylalanine, 1,2,3,4-tetrahydroisoquinoline-3-carboxylic acid, homophenylalanine, 2-amino-4-(2-thienyl)-butyric acid, (Z)-dehydrophenylalanine, (E)-dehydrophenylalanine or 1,3-dioxolan-2-yl-alanine;

$R^1$ denotes isobutyl, benzyl or cyclohexylmethyl;

$R^2$ is hydrogen, methyl, isopropyl or isobutyl;

$R^3$ represents a radical of the formula III in which $R^6$ denotes a five- or six-membered monocyclic or nine- or ten-membered bicyclic heteroaromatic having at least one carbon atom, one or two nitrogen atoms and/or one sulfur or oxygen atom as ring members;

X is —$CF_2$—, —CO— or —$CHR^8$—, where $R^8$ denotes methyl, ethyl, isopropyl, methoxy, ethoxy, isopropoxy, —OH, —$N_3$ or —F;

q and s are, independently of one another, 1, 2 or 3;

r is 0 or 1, with the proviso that if $R^4$ represents a radical of the formula IV with t=2, r is 0; and $R^9$ denotes hydrogen, acetoxymethyl, acetoxyethyl, pivaloyloxymethyl, pivaloyloxyethyl, 2,2-dimethylbutyryloxymethyl, ethoxycarbonyloxymethyl, ethoxycarbonyloxyethyl, tert.-butoxycarbonyloxymethyl or tert.-butoxycarbonyloxyethyl;

as well as the physiologically tolerated salts thereof.

The invention also relates to a process for the preparation of compounds of the formula I, which comprises a fragment with a terminal carboxyl group, or a reactive derivative thereof, being coupled to an appropriate fragment with a free amino group, where appropriate (a) protective group(s) temporarily introduced to protect other functional groups being eliminated, and the compound obtained in this way being converted, where appropriate, into its physiologically tolerated salt.

Fragments of a compound of the formula I with a terminal carboxyl group have the formulae Va and Vb below:

A—OH  (Va)

A—B—OH  (Vb)

Fragments of a compound of the formula I with a terminal amino group have the formulae VIa and VIb below:

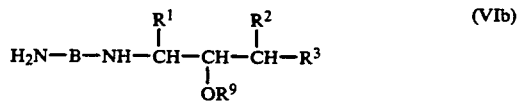  (VIa)

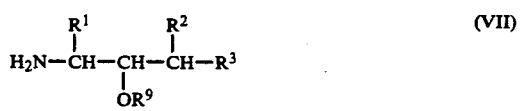  (VIb)

Methods suitable for preparing an amide bond are described for example, in Houben-Weyl, Methoden der organischen Chemie (Methods of Organic Chemistry), volume 15/2; Bodanszky et al., Peptide synthesis, 2nd ed. (Wiley & Son, New York 1976) or Gross, Meienhofer, The Peptides. Analysis, synthesis, biology (Academic Press, New York 1979). The following methods are preferably employed: the active ester method with N-hydroxysuccinimide as ester component, coupling with a carbodiimide such as dicyclohexylcarbodiimide or with propanephosphonic acid anhydride, and the mixed anhydride method with pivaloyl chloride.

The preparation of the optically active amines of the formula VII, which are used as starting compounds,

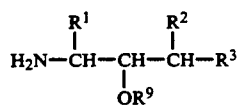  (VII)

in which $R^1$, $R^2$, $R^3$ and $R^9$ are as defined above, is carried out starting from optically active α-amino acids, with retention of the center of asymmetry thereof. A N-protected amino aldehyde is prepared in a known manner for this and is coupled, in an aldol-analogous addition, to an appropriate heteroarylalkyl building block and, after elimination of the N-protective group, yields amino alcohols of the formula VII ($R^9$=H). As an alternative to this, the epoxides are prepared in a manner known per se from the protected amino aldehydes via the allylamines. It is possible either to react these epoxides directly with the appropriate arylalkyl nucleophiles, or initially to open the epoxide with trimethylsilyl chloride and NaI in acetonitrile, and cleave the silyl ether with CsF and protect the iodide with 2,2-dimethoxypropane under acid catalysis as the oxazolidine. This iodide can be reacted with less reactive nucleophiles. The synthesis of arylalkyl-substituted amino alcohols extended by one $CH_2$ group starts, for example, from Boc-ACHPA-OEt (prepared as in J. Med. Chem. 28, 1779 (1985)). N,O-Protection is carried out first, and then reduction of the ester group and finally conversion of the hydroxyl group into a bromide, which can be reacted with arylalkyl nucleophiles under conditions analogous to the electrophiles already mentioned. Examples of suitable arylalkyl nucleophiles are acetylamines and acetylhydrazones. Further compounds of the arylalkyl-substituted amino alcohols with extended $CH_2$ group(s) can be obtained by the general methods customary for chain extension. If the chosen synthetic route results in diastereomers with respect to the center carrying $OR^9$, these can be separated in a manner known per se, for example by fractional crystallization or by chromatography. The diastereomeric purity is checked by HPLC, and the enantiomeric purity can be checked in a known manner by conversion into Mosher derivatives (H.S. Mosher et al., J. org. Chem. 34, 2543 (1969)).

N-Protected amino aldehydes are prepared as described by B. Castro et al. (Synthesis 1983, 676).

The addition of the arylalkyl nucleophiles to the said N-protected electrophiles (protective groups preferably N-tert.-butoxycarbonyl and benzyloxycarbonyl) is carried out in a solvent which is inert to bases, such as ether, THF, toluene, DMF, DMSO or dimethoxyethane.

Bases which can be used to deprotonate the heteroarylalkyl component are alkali metal alcoholates such as potassium tert.-butylate or sodium methylate, alkali metal hydrides such as sodium or potassium hydride, organometallic bases such as n-butyllithium, s-butyllithium, methyllithium or phenyllithium, sodium amide and alkali metal salts of organic nitrogen bases such as lithium diisopropylamide.

It is possible, in an obtainable compound of the formula I, to oxidize a thio group to a sulfinyl or sulfonyl group or a sulfinyl group to a sulfonyl group.

The oxidation to give the sulfonyl group can be carried out with most of the customary oxidizing agents. It is preferable to use those oxidizing agents which selectively oxidize the thio group of sulfinyl group in the presence of other functional groups in the compound of the formula I, for example the amide group and the hydroxyl group, for example aromatic or aliphatic peroxycarboxylic acids, for example perbenzoic acid, monoperphthalic acid, m-chloroperbenzoic acid, peracetic acid, performic acid or trifluoroperacetic acid.

The preliminary and subsequent operations required for the preparation of compounds of the formula I, such as introduction and elimination of protective groups, are known from the literature and described, for example, in T. W. Greene, "Protective Groups in Organic Synthesis". Salts of compounds of the formula I with salt-forming groups are prepared in a manner known per se, for example by reacting a compound of the formula I having a basic group with a stoichiometric amount of a suitable acid. Mixtures of stereoisomers, in particular mixtures of diastereomers, which result when racemic acids A or B are used, can be separated in a manner known per se, by fractional crystallization or by chromatography.

The compounds of the formula I according to the invention have enzyme-inhibiting properties; in particular they inhibit the action of the natural enzyme renin. Renin is a proteolytic enzyme which belongs to the class of aspartyl proteases and is secreted following various stimuli (volume depletion, sodium deficiency, β-receptor stimulation) from the juxtaglomerular cells of the kidney into the blood circulation. There it eliminates the decapeptide angiotensin I from the angiotensinogen secreted by the liver. The former is converted by angiotensin converting enzyme (ACE) into angiogensin II. Angiotensin II plays a considerable part in the regulation of blood pressure because it directly increases the blood pressure by vasoconstriction. In addition, it stimulates the secretion of aldolsterone from the adrenal and, via the inhibition of sodium excretion, in this way increases the extracellular fluid volume, which in turn contributes to an increase in blood pressure. Inhibitors of the enzymatic activity of renin bring about a diminished formation of angiotensin I, which results in a diminished formation of angiotensin II. The reduction in the concentration of this active peptide hormone is the direct cause of the action of renin inhibitors to lower blood pressure.

The activity of renin inhibitors can be checked by in vitro tests. These entail measurement of the reduction in the formation of angiotensin I in various sytems (human plasma, porkine renin). For this purpose, for example, human plasma, which contains both renin and angiotensinogen, is incubated at 37° C. with the compound to be tested. The concentration of angiotensin I formed during the incubation is subsequently measured using a radioimmunoassay. The compounds of the general formula I described in the present invention show, in the in vitro tests used, inhibitory actions at concentrations of about $10^{-5}$ to $10^{-10}$ mol/l.

Renin inhibitors bring about a lowering of blood pressure in salt-depleted animals. Since human renin differs from the renin of other species, primates (marmosets, rhesus monkeys) are employed for in vivo testing of renin inhibitors. Primate renin and human renin are substantially homologous in their sequences. Endogenous secretion of renin is stimulated by i.v. injection of furosemide. The test compounds are subsequently administered by continuous infusion, and their effect on blood pressure and heart rate is measured. In the tests, the compounds of the present invention are active in an i.v. dose range of about 0.1–5 mg/kg. The compounds of the general formula I described in the present invention can be used as antihypertensives and for the treatment of cardiac insufficiency.

Hence the invention also relates to the use of compounds of the formula I as medicines and to pharmaceutical compositions which contain these compounds, as well as to a process for the preparation thereof. The preferred use is in primates, especially in humans.

Pharmaceutical products contain an effective amount of the active substance of the formula I together with a pharmaceutically utilizable inorganic or organic vehicle. Administration can be intransally, intravenously, subcutaneously or orally. The dosage of the active substance depends on the warm-blooded species, the body weight and age and on the mode of administration.

The pharmaceutical products of the present invention are prepared in dissolution, mixing, granulating or coating processes known per se.

For a form for oral administration, the active compounds are mixed with the additives customary for this purpose, such as vehicles, stabilizers or inert diluents, and converted by customary methods into suitable dosage forms, such as tablets, coated tablets, hard gelatin capsules, aqueous, alcoholic or oily suspensions or aqueous, alcoholic or oily solutions. Examples of inert excipients which can be used are gum arabic, magnesia, magnesium carbonate, potassium phosphate, lactose, glucose, magnesium stearyl fumarate or starch, especially cornstarch. This preparation can be both as dry and wet granules. Examples of suitable oily vehicles or solvents are plant or animal oils, such as sunflower oil and fish liver oil.

For subcutaneous or intravenous administration, the active compounds or the physiologically tolerated salts thereof are converted into solutions, suspensions or emulsions, if desired with the substances customary for this purpose, such as stabilizers, emulsifiers or other auxiliaries. Examples of suitable solvents are: water, physiological saline solutions or alcohols, for example ethanol, propanediol or glycerol, as well as sugar solutions such as glucose or mannitol solutions, or else a mixture of the various solvents mentioned.

List of abbreviations used:
ACHPA: [3S,4S]-4-Amino-3-hydroxy-5-cyclohexyl-pentanoic acid
Boc: tert.-Butoxycarbonyl
BuLi: Butyllithium TLC: Thin-layer chromatography
DCC: Dicyclohexylcarbodiimide
DCI: Desorption Chemical Ionization
DIP: Diisopropyl ether
DNP: 2,4-Dinitrophenyl
DME: Dimethoxyethane
DMF: Dimethylformamide
DOPA: 3,4-Dihydroxyphenylalanine
EA: Ethyl acetate
EI: Electron Impact
FAB: Fast atom bombardment
H: n-Hexane
HOBt: 1-Hydroxybenzotriazole
M: Molecular peak
MeOH: Methanol
MS: Mass spectrum
MTB: Methyl tert.-butyl ether
NEM: N-Ethylmorpholine
R.T.: Room temperature
m.p.: Melting point
THF: Tetrahydrofuran The other abbreviations used for amino acids correspond to the three-letter code which is customary in peptide chemistry and is described in, for example, Europ. J. Biochem. 138, 9–37 (1984). Unless expressly indicated otherwise, the amino acids are always of the L configuration.

The examples which follow serve to illustrate the present invention without restricting it to them.

EXAMPLE 1

N-(2(R)-Benzyl-3-tert.-butylsulfonyl-propionyl)-His-1(S)-cyclohexylmethyl-2(S)-hydroxy-5-(2-pyridyl)-pentylamide and N-(2(S)-benzyl-3-tert.-butylsulfonyl-propionyl)-His-1(S)-cyclohexylmethyl-2(S)-hydroxy-5-(2-pyridyl)-pentylamide 240 mg of N-2(R,S)-benzyl-3-tert.-butylsulfonyl-propionyl)-His(DNP)-1(S)-cyclohexylmethyl-2(S)-hydroxy-5-(2-pyridyl)-pentylamide are stirred with 100 mg of thiophenol in 5 ml of acetonitrile at room temperature for 4 hours. The mixture is concentrated and then chromatographed on silica gel using dichloromethane/methanol (12:1) saturated with concentrated $NH_3$.

50 mg of the less polar (R) isomer and 40 mg of the more polar (S) isomer are obtained.

(R) isomer: $R_f$ 0.16 MS (FAB): 680 (M+1)
(S) isomer: $R_f$ 0.1 MS (FAB): 680 (M+1)

a)
N-(2(R,S)-Benzyl-3-tert.-butylsulfonyl-propionyl)-His-(DNP)-1(S)-cyclohexylmethyl-2(S)-hydroxy-5-(2-pyridyl)-pentylamide 220 mg of H-His(DNP)-1(S)-cyclohexylmethyl-2(S)-hydroxy-5-(2-pyridyl)-pentylamide are stirred with 113 mg of 2-(R,S)-benzyl-3-tert.-butylsulfonylpropionic acid, 82 mg of DCC, 61 mg of HOBt and 92 mg of NEM in 4 ml of DMF at room temperature for 20 hours. The mixture is filtered and then diluted with EA and washed 1× each with 3% $NaHCO_3$, 10% citric acid, 3% $NaHCO_3$ and saturated NaCl, dried with $Na_2SO_4$ and concentrated. 240 mg of the title compound are obtained as a resin (mixture of isomers, $R_f$ values 0.6 and 0.55 ($CH_2Cl_2$/MeOH=10:1).

b)
H-His(DNP)-1(S)-cyclohexylmethyl-2(S)-hydroxy-5-(2-pyridyl)-pentylamide hydrochloride 230 mg of Boc-His(DNP)-1(S)-cyclohexylmethyl-2(S)-hydroxy-5-(2-pyridyl)-pentylamide are stirred in 5 ml of saturated DME/HCl for 90 minutes and subsequently concentrated. 220 mg of the title compound are obtained as a resin.

$R_f$($CH_2Cl_2$/MeOH=10:1) 0.1.

c)
Boc-His(DNP)-1(S)-cyclohexylmethyl-2(S)-hydroxy-5-(2-pyridyl)-pentylamide 550 μl of pivaloyl chloride are added dropwise, at −5° C., to 1.9 g of Boc-His(DNP)-OH, 360 μl of pyridine and 620 μl of N-ethylpiperidine in 50 ml of $CH_2Cl_2$. After 10 minutes at −5° C., the mixture is stirred at +10° C. for 10 minutes. It is again cooled to −5° C. and then 1.3 g of 1(S)-cyclohexylmethyl-2(S)-hydroxy-5-(2-pyridyl)-pentylamine (prepared from 1.7 g of 3-Boc-4(S)-cyclohexylmethyl-2,2-dimethyl-5-(3-(2-pyridyl)propyl)oxazolidine by the process described under b) and subsequent liberation with $Na_2CO_3$) in 20 ml of $CH_2Cl_2$ are added. After 1 hour at −5° C., the mixture is left to stand at room temperature for 16 hours. 50 ml of saturated $Na_2CO_3$ solution are added, and the mixture is extracted 3 times with EA. The combined organic extracts are dried over $Na_2SO_4$ and concentrated. Chromatography on silica gel (EA/MeOH 10:1) yields the title compound.

$R_f$(EA/MeOH 10:1)=0.25; MS (FAB)=680 (M+1).

d)
3-Boc-4(S)-cyclohexylmethyl-2,2-dimethyl-5-(3-(2-pyridyl)propyl)oxazolidine 367 μl of 2-picoline are deprotonated with n-BuLi in anhydrous THF. 500 mg of 3-Boc-4(S)-cyclohexylmethyl-2,2-dimethyl-5-(2-bromoethyl)oxazolidine in 10 ml of THF are added to the deep-red solution at −50° C. After 15 minutes, $H_2O$ is added, and the mixture is extracted 3 times with EA. The organic phases are dried with $Na_2SO_4$ and then concentrated, and the residue is chromatographed on silica gel (eluent: toluene/EA 3:1).

$R_f$(toluene/EA 3:1)=0.25; MS=417 (M+1).

e)
3-Boc-4(S)-cyclohexylmethyl-2,2-dimethyl-5-(2-bromoethyl)oxaxolidine 1.6 ml of diethyl azodicarboxylate are added dropwise, at 20° C. under argon, to 690 mg of 3-Boc-1(S)-cyclohexylmethyl-2,2-dimethyl-5-(2-hydroxyethyl)-oxazolidine, 2.6 g of triphenylphosphine and 1.6 g of pyridinium bromide in 15 ml of $CH_2Cl_2$. After 16 hours at room temperature, $H_2O$ is added, and the mixture is diluted with 100 ml of $CH_2Cl_2$. The organic phase is washed twice with saturated $NaHCO_3$ solution and once with saturated NaCl solution. The organic phase is dried with $Na_2SO_4$ and concentrated, and the residue is taken up in a little EA and filtered to remove $PPh_3$. Purification on silica gel yields the title compound (eluent: H/EA 15:1).

$R_f$(H/EA 15:1)=0.3; MS 404 (M).

f) 3-Boc-4(S)-cyclohexylmethyl-2,2-dimethyl-5-(2-hydroxyethyl)-oxazolidine 10 g of Boc-ACHPA-OEt, 500 mg of p-toluenesulfonic acid and 7.2 ml of dimethoxypropane are heated in 160 ml of toluene at 80° C. under argon for 2 hours. The mixture is subsequently concentrated. The residue is added dropwise at 0° C. to a suspension of 2 g of LiAlH$_4$ in 200 ml of THF. After 2.5 hours at 0° C., 100 ml of 5% strength NaHSO$_4$ solution are added, and the mixture is extracted 3 times with EA. The combined organic phases are washed once with saturated NaHCO$_3$ solution. They are dried with Na$_2$SO$_4$ and then concentrated and chromatographed (eluent: H/EA 2:1).

R$_f$(H/EA 4:1)=0.1; MS=342 (M+1).

EXAMPLE 2

N-(2(R)-Benzyl-3-cyclohexylsulfonyl-propionyl)-His-1(S)-cyclohexylmethyl-2(S)-hydroxy-5-(2-pyridyl)-pentylamide and N-(2(S)-Benzyl-3-cyclohexylsulfonyl-propionyl)-His-1(S)-cyclohexylmethyl-2(S)-hydroxy-5-(2-pyridyl)-pentylamide 270 mg of N-2(R,S)-benzyl-3-cyclohexylsulfonyl-propionyl)-His(DNP)-1-(S)-cyclohexylmethyl)-2(S)-hydroxy-5-(2-pyridyl)-pentylamide are stirred with 100 mg of thiophenol in 3 ml of acetonitrile for 2 hours. The mixture is concentrated and then chromatographed on silica gel using dichloromethane/methanol/concentrated NH$_3$ (10:1:0.1).

The following are obtained:
80 mg of less polar (R) isomer (HPLC: t$_R$ 11.0 min (Nucleosil C$_{18}$ (7µ)), mobile phase CH$_3$CN/H$_2$O 34:66 (0.1% TFA) 1.5 ml/min), and
40 mg of more polar (S) isomer, melting point 158°–161° C. (HPLC: t$_R$=14.5 min, same conditions as for (R) isomer)

a) N-2(R,S)-Benzyl-3-cyclohexylsulfonyl-propionyl-His(DNP)-1-(S)-cyclohexylmethyl-2(S)-hydroxy-5-(2-pyridyl)-pentylamide In analogy to the procedure indicated in Example 1a), 180 mg of H-His-(DNA)-1(S)-cyclohexylmethyl-2(S)-hydroxy-5-(2-pyridyl)-pentylamide are reacted with 60 mg of 2(R,S)-benzyl-3-cyclohexylsulfonylpropionic acid. 280 mg of the title compound are obtained as a yellowish resin.

R$_f$(SiO$_2$; CH$_2$Cl$_2$/MeOH 10:1)=0.5.

b) 2-(R,S)-Benzyl-3-cyclohexylsulfonylpropionic acid 3.2 g of ethyl 2-(R,S)-benzyl-3-cyclohexylsulfonyl-propionate are refluxed in 50 ml of 5 N HCl for 8 hours. The mixture is extracted with dichloromethane, and the extract is dried with Na$_2$SO$_4$. The concentration results in 1.1 g of the title compound as an oil.

c) Ethyl 2-(R,S)-benzyl-3-cyclohexylsulfonylpropionate 4.1 g of ethyl 2-(R,S)-benzyl-3-cyclohexylthiopropionate in 50 ml of dry dichloromethane are mixed with 6.9 g of 3-chloroperbenzoic acid. After 3 hours at R.T., a further 4 g of 3-chloroperbenzoic acid are added. After a further 4 hours, the mixture is filtered with suction, and the filtrate is washed 1× each with saturated NaHSO$_3$ solution and Na$_2$CO$_3$ solution, dried with MgSO$_4$ and concentrated. 3.2 g of the title compound are obtained as an oil.

R$_f$(SiO$_2$, ethyl acetate/cyclohexane (1:1))=0.55.

d) Ethyl 2-(R,S)-benzyl-3-cyclohexylthiopropionate 3 g of ethyl 2-benzylacrylate are dissolved together with 1.8 g of cyclohexyl mercaptan and 0.2 g of sodium hydride in 50 ml of dry ethanol. After 48 hours at room temperature, the mixture is acidified with 2N HCL and extracted with ether. 4.1 g of the title compound are obtained as an oil.

Rf (SiO$_2$; ethyl acetate/cyclohexane 1:4)=0.16.

e) Ethyl 2-benzylacrylate 127.6 g of diethyl 2-benzylmalonate are refluxed with 20.4 g of NaOH in 1 l of dry ethanol. After 8 hours, the solvent is removed, the residue is taken up in 2N HCl, and the solution is extracted with ether. The organic phase is dried and concentrated. The residue is cooled, and 51.2 ml of diethylamine and 43.7 ml of 36% strength formaldehyde solution are added. The mixture is left to stand overnight and then extracted with ether, and the extracts are dried and concentrated. The product is distilled.

Boiling point 70° C. (0.01 mm); yield 56 g.

EXAMPLE 3

N-(2(R)-Benzyl-3-phenylsulfonyl-propionyl)-His-1(S)-cyclohexylmethyl-2(S)-hydroxy-5-(2-pyridyl)-pentylamide and N-(2(S)-benzyl-3-phenylsulfonyl-propionyl)-His-1(S)-cyclohexylmethyl-2(S)-hydroxy-5-(2-pyridyl)-pentylamide 320 mg of N-(2(R,S)-benzyl-3-phenylsulfonyl-propionyl)-His(DNP)-1(S)-cyclohexylmethyl-2(S)-hydroxy-5-(2-pyridyl)-pentylamide are stirred with 120 mg of thiophenol in 3 ml of acetonitrile for 2 hours. Chromatography on silica gel with dichloromethane/methanol/concentrated NH$_3$ (10:1:0.1) yields 50 mg of (R) isomer and 60 mg of (S) isomer.

(R) isomer: t$_R$ (HPLC, conditions as Example 2): 8.5 min (S) isomer: t$_R$=11.8 min.

a) N-(2(R,S)-Benzyl-3-phenylsulfonyl-propionyl)-His(DNP)-1(S)-cyclohexylmethyl-2(S)-hydroxy-5-(2-pyridyl)-pentylamide In analogy to the procedure indicated in Example 1a), 180 mg of H-His(CNP)-1(S)-cyclohexylmethyl-2(S)-hydroxy-5-(2-pyridyl)-pentylamide are reacted with 60 mg of 2(R,S)-benzyl-3-phenylsulfonylpropionic acid. 320 mg of the title compound are obtained.

R$_f$(SiO$_2$, CH$_2$Cl$_2$/MeOH 10:1)=0.45.

b) 2-(R,S)-Benzyl-3-phenylsulfonylpropionic acid

Prepared from thiophenol and ethyl 2-benzylacrylate in analogy to the procedures indicated in Example 2b-d.

R$_f$(SiO$_2$; CH$_2$Cl$_2$/MeOH 10:1)=0.3.

EXAMPLE 4

N-[2-(R)-(4-Methoxy-benzyl)-3-tert.-butylsulfonyl-propionyl]-His-1(S)-cyclohexylmethyl-2(S)-hydroxy-5-(2-pyridyl)-pentylamide and N-[2-(S)-(4-Methoxy-benzyl)-3-tert.-butylsulfonyl-propionyl]-His-1(S)-cyclohexylmethyl-2(S)-hydroxy-5-(2-pyridyl)-pentylamide 94 mg of N- 2-(R,S)-(4-methoxy-benzyl)-3-tert.butylsulfonylpropionyl-His(DNP)-1-(S)-cyclohexylmethyl-2(S)-hydroxy-5-(2-pyridyl)-pentylamide are stirred with 37 μl of thiophenol in 4 ml of acetonitrile for 2 hours. The residue from concentration is chromatographed on silica gel (mobile phase: $CH_2Cl_2$/MeOH (10:1)). 22 mg of (R) isomer and 29 mg of (S) isomer are obtained.

(R) isomer: $R_f$ 0.17 (ethyl acetate/MeOH=10:1); MS(FAB): 710 (M+1)

(S) isomer: $R_f$ 0.11 (ethyl acetate/MeOH=10:1); MS(FABh 710 (M+1)

a)
N-[2-(R,S)-(4-Methoxybenzyl)-3-tert.-butylsulfonylpropionyl]-His(DNP)-1-(S)-cyclohexylmethyl-2(S)-hydroxy-5-(2-pyridyl)-pentylamide In analogy to the procedure indicated in Example 1a), 130 mg of H-His(DNP)-1(S)-cyclohexylmethyl-2(S)-hydroxy-5-(2-pyridyl)-pentylamide are reacted with 60 mg of 2-(R,S)-(4-methoxybenzyl)-3-tert.-butylsulfonylpropionic acid. 94 mg of the title compound are obtained as a mixture of isomers.

$R_f$(SiO2; $CH_2Cl_2$/MeOH=10:1) 0.43 and 0.36.

b)
2-(R,S)-(4-Methoxybenzyl)-3-tert.-butylsulfonylpropionic acid

Prepared from tert.-butyl mercaptan and diethyl 2-(4-methoxybenzyl)malonate in analogy to the procedures indicated in Example 2b-e.

$R_f$(SiO2; $CH_2Cl_2$/MeOH 10:2)=0.22.

EXAMPLE 5

N-[2-(R,S)-(2-Thienyl-methyl)-3-tert.-butylsulfonyl-propionyl]-His-1-(S)-cyclohexylmethyl-2-(S)-hydroxy-5-(2-pyridyl)-pentylamide Prepared in analogy to Example 1 from N-[2-(R,S)-(2-thienylmethyl)-3-tert.-butylsulfonyl-propionyl]-His(DNP)-1-(S)-cyclohexylmethyl-2-(S)-hydroxy-5-(2-pyridyl)-pentylamide and thiophenol.

$R_f$(SiO2; ethyl acetate/methanol 5:1)=0.1.
MS(FAB)=686 (M+1)

a)
N-[2-(R,S)-(2-Thienylmethyl)-3-tert.-butylsulfonylpropionyl]-His(DNP)-1-(S)-cyclohexyl-2-(S)-hydroxy-5-(2-pyridyl)-pentylamide Prepared in analogy to the procedure indicated in Example 1a) from H-His(DNP)-1-(S)-cyclohexylmethyl-2-(S)-hydroxy-5-(2-pyridyl)-pentylamide and (R,S)-2-(2-thienylmethyl)-3-tert.-butylsulfonylpropionic acid.

b)
(R,S)-2-(2-Thienylmethyl)-3-tert.-butylsulfonylpropionic acid

Prepared from diethyl 2-(2-thienylmethyl)malonate and tert.-butyl mercaptan in analogy to the procedures indicated in Example 2b-e.

EXAMPLE 6

N-[2-(R)-Benzyl-3-(2-furylmethylsulfonyl)-propionyl]-His-1(S)-cyclohexylmethyl-2(S)-hydroxy-5-(2-pyridyl)-pentylamide and N-[2-(S)-Benzyl-3-(2-furylmethylsulfonyl)-propionyl]-His-1(S)-cyclohexylmethyl-2-(S)-hydroxy-5-(2-pyridyl)-pentylamide Prepared in analogy to the procedure indicated in Example 1 from N-[2-(R,S)-benzyl-3-(2-furylmethylsulfonyl)-propionyl]-His(DNP)-1-(S)-cyclohexylmethyl-2(S)-hydroxy-5-(2-pyridyl)-pentylamide and thiophenol.

(R) isomer: $R_f$ (SiO2; methanol/ethyl acetate 1:5)=0.25
MS(FAB): 704 (M+1)

(S) isomer: $R_f$ (SiO2; methanol/ethyl acetate 1:5)=0.15
MS(FAB): 704 (M+1)

a)
N-[2-(R,S)-Benzyl-3-(2-furylmethylsulfonyl)-propionyl]-His (DNP)-1-(S)-cyclohexylmethyl-2-(S)-hydroxy-5-(2-pyridyl)-pentylamide Prepared in analogy to the procedure indicated in Example 1a) from H-His(DNP)-1(S)-cyclohexylmethyl-2-(S)-hydroxy-5-(2-pyridyl)-pentylamide and (R,S)-2-benzyl-3-(2-furylmethylsulfonyl)-propionic acid.

b) (R,S)-2-Benzyl-3-(2-furylmethylsulfonyl)-propionic acid

Prepared in analogy to the procedures indicated in Example 2b-d from ethyl 2-benzylacrylate and 2-furylmethyl mercaptan.

We claim:

1. A compound of the formula I:

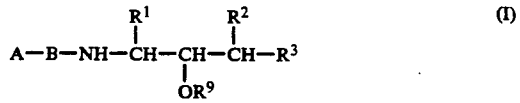

wherein:

A is a radical of the formula II:

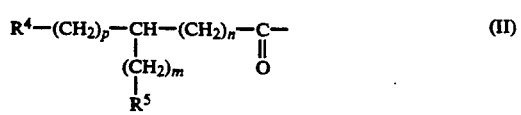

in which $R^4$ is a radical of the formula IV:

wherein $R^7$ is $(C_1–C_{10})$-alkyl which is unsubstituted or substituted by one or more functional groups selected from the group consisting of oxo, hydroxyl, (C$_1$-C$_6$)-alkoxy and phenyloxy; (C$_1$-C$_6$)-alkanoyloxy; halogen; hydroxysulfonyloxy; carboxyl; (C$_1$-C$_4$)-alkoxycarbonyl; carbamoyl, mono-(C$_1$-C$_4$)-alkylcarbamoyl or di-(C$_1$-C$_4$)-alkyl-carbamoyl; cyano; amino; mono-(C$_1$-C$_4$)-alkylamino or di-(C$_1$-C$_4$)-alkylamino; acylamino or substituted amino in which the amino group is part of a pyridyl group; (C$_2$-C$_8$)-alkenyl which is unsubstituted or substituted by one or more functional groups selected from the group consisting of oxo, hydroxyl, (C$_1$-C$_6$)-alkoxy and phenyloxy or (C$_2$-C$_8$)-alkynyl which is optionally substituted by one or more functional groups selected from the group consisting of oxo, hydroxyl, (C$_1$-C$_6$)-alkoxy and phenyloxy; hydroxyl; (C$_1$-C$_6$)-alkoxy; (C$_3$-C$_8$)-cycloalkyl; (C$_5$-C$_{10}$)-bicycloalkyl; (C$_8$-C$_{10}$)-tricycloalkyl; (C$_3$-C$_8$)-cycloalkyl-(C$_1$-C$_{10}$)-alkyl; (C$_6$-C$_{14}$)-aryl, (C$_6$-C$_{14}$)-aryloxy or (C$_6$-C$_{14}$)-aryl-(C$_1$-C$_{10}$)-alkyl, which are optionally substituted in the aryl moiety by one or two identical or different radicals selected from the group consisting of F, Cl, Br, hydroxyl, (C$_1$-C$_7$)-alkoxy, (C$_1$-C$_7$)-alkyl, (C$_1$-C$_7$)-alkoxycarbonyl, amino and trifluoromethyl; pyridyl; or amino, mono-(C$_1$-C$_4$)-alkylamino, di-(C$_1$-C$_4$)-alkylamino, acylamino or substituted amino in which the amino is part of a pyridyl group; and
t is 2;
R$^5$ is phenyl; 2-, 3- or 4-pyridyl; or 1- or 2-naphthyl; each of which is optionally substituted by a radical selected from the group consisting of hydroxyl, (C$_1$-C$_4$)-alkyl, (C$_1$-C$_4$)-alkoxy, Cl, F, Br, nitro, amino, acetamino, and trifluoromethyl or by a methylenedioxy radical;
m is 1;
n is 0 or 1;
p is 0, 1 or 2;
B is a radical, which is linked N-terminal to A and C-terminal

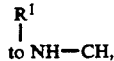
to NH—CH, of an amino acid selected from the group consisting of phenylalanine, histidine, tyrosine, tryptophan, methionine, leucine, isoleucine, asparagine, aspartic acid, β-2-thienylalanine, β-3-thienylalanine, β-2-furylalanine, β-3-furylalanine, lysine, ornithine, valine, alanine, 2,4-diaminobutyric acid, arginine, 4-chlorophenylalanine, methionine sulfone, methionine sulfoxide, 2-pyridylalanine, 3-pyridylalanine, cyclohexylalanine, cyclohexylglycine, im-methylhistidine, O-methyltyrosine, O-benzyltyrosine, O-tertbutyltyrosine, phenylglycine, 1-naphthylalanine, 2-naphthylalanine, 4-nitrophenylalanine, norvaline, β-2-benzo[b]thienylalanine, β-3-benzo[b]thienylalanine, 2-fluorophenylalanine, 3-fluorophenylalanine, 4-fluorophenylalanine, norleucine, cysteine, S-methylcysteine, 1,2,3,4-tetrahydroisoquinoline-3-carboxylic acid, homophenylalanine, DOPA, O-dimethyl-DOPA, 2-amino-4-(2-thienyl)butyric acid, benzodioxol-5-ylalanine, N-methyl-histidine, 2-amino-4-(3-thienyl)butyric acid, 3-(2-thienyl)serine, (Z)-dehydrophenylalanine, (E)-dehydrophenylalanine, 1,3-dioxolan-2-ylalanine, N-pyrrolylalanine, and 1-, 3- or 4-pyrazolylalanine;
R$^1$ is hydrogen, (C$_1$-C$_{10}$)-alkyl, (C$_4$-C$_7$)-cycloalkyl, (C$_4$-C$_7$)-cycloalkyl-(C$_1$-C$_4$)-alkyl, (C$_6$-C$_{14}$)-aryl, (C$_6$-C$_{14}$)-aryl-(C$_1$-C$_4$)-alkyl or 1,3-dithiolan-2-yl-(C$_1$-C$_4$)-alkyl;
R$^2$ is hydrogen;
R$^3$ is a radical of the formula III:

in which
R$^6$ is pyridyl; and
q and s is each, independently of one another, 0, 1 or 2; and
R$^9$ is hydrogen;
and physiologically tolerated salts thereof.

2. A compound of the formula I according to claim 1, wherein:
said amino acid of the radical B is selected from the group consisting of phenylalanine, histidine, tyrosine, β-2-thienylalanine, β-3-thienylalanine, valine, methyltyrosine, norvaline, β-2-benzo[b]thienylalanine and β-3-benzo[b]-thienylalanine; and
R$^1$ is (C$_4$-C$_7$)-cycloalkyl-(C$_1$-C$_4$)-alkyl.

3. A pharmaceutical composition comprising an amount effective to inhibit renin of a compound of formula I or a pharmaceutically acceptable salt thereof:

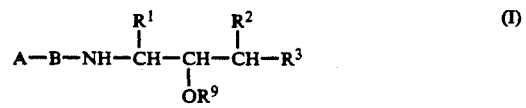

wherein:
A is a radical of the formula II:

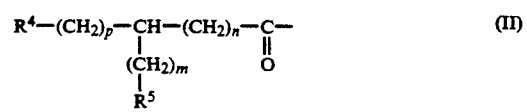

in which
R$^4$ is a radical of the formula IV:

wherein
R$^7$ is (C$_1$-C$_{10}$)-alkyl which is unsubstituted or substituted by one or more functional groups selected from the group consisting of oxo, hydroxyl, (C$_1$-C$_6$)-alkoxy and phenyloxy; (C$_1$-C$_6$)-alkanoyloxy; halogen; hydroxysulfonyloxy; carboxyl; (C$_1$-C$_4$)-alkoxycarbonyl; carbamoyl, mono-(C$_1$-C$_4$)-alkylcarbamoyl or di-(C$_1$-C$_4$)-alkyl-carbamoyl; cyano; amino; mono-(C$_1$-C$_4$)-alkylamino or di-(C$_1$-C$_4$)-alkylamino; acylamino or substituted amino in which the amino group is part of a pyridyl group; (C$_2$-C$_8$)-alkenyl which is unsubstituted or substituted by one or more functional groups selected from the group consisting of oxo, hydroxyl, (C$_1$-C$_6$)-alkoxy and phenyloxy or (C$_2$-C$_8$)-alkynyl which is optionally substituted by one or more functional groups selected from the group consisting of oxo, hydroxyl, (C$_1$-C$_6$)-alkoxy and phenyloxy; hydroxyl; (C$_1$-C$_6$)-alkoxy; (C$_3$-C$_8$)-cycloalkyl; (C$_5$-C$_{10}$)-bicycloalkyl; (C$_8$-C$_{10}$)-tricycloalkyl; (C$_3$-C$_8$)-cycloalkyl-(C$_1$-C$_{10}$)-alkyl; (C$_6$-C$_{14}$)-aryl, (C$_6$-C$_{14}$)-aryloxy or (C$_6$-C$_{14}$)-aryl-(C$_1$-C$_{10}$)- alkyl, which are optionally substituted in the aryl moiety by one or two identical or different radicals selected from the group consisting of F, Cl, Br, hydroxyl, $(C_1-C_7)$-alkoxy, $(C_1-C_7)$-alkyl, $(C_1-C_7)$-alkoxycarbonyl, amino and trifluoromethyl; pyridyl; or amino, mono-$(C_1-C_4)$-alkylamino, di-$(C_1-C_4)$-alkylamino, acylamino or substituted amino in which the amino is part of a pyridyl group; and t is 2;

$R^5$ is phenyl; 2-, 3- or 4-pyridyl; or 1- or 2-naphthyl; each of which is optionally substituted by a radical selected from the group consisting of hydroxyl, $(C_1-C_4)$-alkyl, $(C_1-C_4)$-alkoxy, Cl, F, Br, nitro, amino, acetamino, and trifluoromethyl or by a methylenedioxy radical;

m is 1;

n is 0 or 1;

p is 0, 1 or 2;

B is a radical, which is linked N-terminal to A and C-terminal

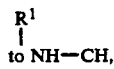
to NH—CH, of an amino acid selected from the group consisting of phenylalanine, histidine, tyrosine, tryptophan, methionine, leucine, isoleucine, asparagine, aspartic acid, β-2-thienylalanine, β-3-thienylalanine, β-2-furylalanine, β-3-furylalanine, lysine, ornithine, valine, alanine, 2,4-diaminobutyric acid, arginine, 4-chlorophenylalanine, methionine sulfone, methionine sulfoxide, 2-pyridylalanine, 3-pyridylalanine, cyclohexylalanine, cyclohexylglycine, im-methylhistidine, O-methyltyrosine, O-benzyltyrosine, O-tertbutyltyrosine, phenylglycine, 1-naphthylalanine, 2-naphthylalanine, 4-nitrophenylalanine, norvaline, β-2-benzo[b]thienylalanine, β-3-benzo[b]-thienylalanine, 2-fluorophenylalanine, 3-fluorophenylalanine, 4-fluorophenylalanine, norleucine, cysteine, S-methylcysteine, 1,2,3,4-tetrahydroisoquinoline-3-carboxylic acid, homophenylalanine, DOPA, O-dimethyl-DOPA, 2-amino-4-(2-thienyl)butyric acid, benzodioxol-5-ylalanine, N-methyl-histidine, 2-amino-4-(3-thienyl)butyric acid, 3-(2-thienyl)serine, (Z)-dehydrophenylalanine, (E)-dehydrophenylalanine, 1,3-dioxolan-2-ylalanine, N-pyrrolylalanine, and 1-, 3- or 4-pyrazolylalanine;

$R^1$ is hydrogen, $(C_1-C_{10})$-alkyl, $(C_4-C_7)$-cycloalkyl, $(C_4-C_7)$-cycloalkyl-$(C_1-C_4)$-alkyl, $(C_6-C_{14})$-aryl, $(C_6-C_{14})$-aryl-$(C_1-C_4)$-alkyl or 1,3-dithiolan-2-yl-$(C_1-C_4)$-alkyl;

$R^2$ is hydrogen;

$R^3$ is a radical of the formula III:

$$-(CH_2)_q-(CH_2)_s-R^6 \qquad (III)$$

in which $R^6$ is pyridyl; and q and s is each, independently of one another, 0, 1 or 2; and $R^9$ is hydrogen.

4. A pharmaceutical composition according to claim 3, wherein in said compound of the formula I: said amino acid of the radical B is selected from the group consisting of phenylalanine, histidine, tyrosine, β-2-thienylalanine, β-3-thienylalanine, valine, methyltyrosine, norvaline, β-2-benzo[b]thienylalanine and β-3-benzo[b]-thienylalanine; and $R^1$ is $(C_4-C_7)$-cycloalkyl-$(C_1-C_4)$-alkyl.

5. A method of inhibiting renin comprising administering to a patient an amount effective to inhibit renin of a compound of formula I or a pharmaceutically acceptable salt thereof:

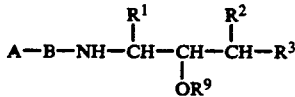

wherein:

A is a radical of the formula II:

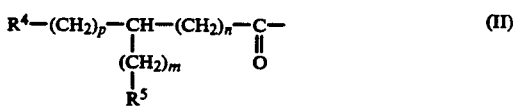

in which $R^4$ is a radical of the formula IV:

wherein $R^7$ is $(C_1-C_{10})$-alkyl which is unsubstituted or substituted by one or more functional groups selected from the group consisting of oxo, hydroxyl, $(C_1-C_6)$-alkoxy and phenyloxy; $(C_1-C_6)$-alkanoyloxy; halogen; hydroxysulfonyloxy; carboxyl; $(C_1-C_4)$-alkoxycarbonyl; carbamoyl, mono-$(C_1-C_4)$-alkylcarbamoyl or di-$(C_1-C_4)$-alkyl-carbamoyl; cyano; amino; mono-$(C_1-C_4)$-alkylamino or di-$(C_1-C_4)$-alkylamino; acylamino or substituted amino in which the amino group is part of a pyridyl group; $(C_2-C_8)$-alkenyl which is unsubstituted or substituted by one or more functional groups selected from the group consisting of oxo, hydroxyl, $(C_1-C_6)$-alkoxy and phenyloxy or $(C_2-C_8)$-alkynyl which is optionally substituted by one or more functional groups selected from the group consisting of oxo, hydroxyl, $(C_1-C_6)$-alkoxy and phenyloxy; hydroxyl; $(C_1-C_6)$-alkoxy; $(C_3-C_8)$-cycloalkyl; $(C_5-C_{10})$-bicycloalkyl; $(C_8-C_{10})$-tricycloalkyl; $(C_3-C_8)$-cycloalkyl-$(C_1-C_{10})$-alkyl; $(C_6-C_{14})$-aryl, $(C_6-C_{14})$-aryloxy or $(C_6-C_{14})$-aryl-$(C_1-C_{10})$-alkyl, which are optionally substituted in the aryl moiety by one or two identical or different radicals selected from the group consisting of F, Cl, Br, hydroxyl, $(C_1-C_7)$-alkoxy, $(C_1-C_7)$-alkyl, $(C_1-C_7)$-alkoxycarbonyl, amino and trifluoromethyl; pyridyl; or amino, mono-$(C_1-C_4)$-alkylamino, di-$(C_1-C_4)$-alkylamino, acylamino or substituted amino in which the amino is part of a pyridyl group; and t is 2;

$R^5$ is phenyl; 2-, 3- or 4-pyridyl; or 1-or 2-naphthyl; each of which is optionally substituted by a radical selected from the group consisting of hydroxyl, $(C_1-C_4)$-alkyl, $(C_1-C_4)$-alkoxy, Cl, F, Br, nitro, amino, acetamino, and trifluoromethyl or by a methylenedioxy radical;

m is 1;

n is 0 or 1;

p is 0, 1 or 2;

B is a radical, which is linked N-terminal to A and C-terminal

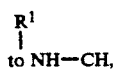

of an amino acid selected from the group consisting of phenylalanine, histidine, tyrosine, tryptophan, methionine, leucine, isoleucine, asparagine, aspartic acid, β-2-thienylalanine, β-3-thienylalanine, β-2-furylalanine, β-3-furylalanine, lysine, ornithine, valine, alanine, 2,4-diaminobutyric acid, arginine, 4-chlorophenylalanine, methionine sulfone, methionine sulfoxide, 2-pyridylalanine, 3-pyridylalanine, cyclohexylalanine, cyclohexylglycine, im-methylhistidine, O-methyltyrosine, O-benzyltyrosine, O-tertbutyltyrosine, phenylglycine, 1-naphthylalanine, 2-naphthylalanine, 4-nitrophenylalanine, norvaline, β-2-benzo[b]thienylalanine, β-3-benzo[b]thienylalanine, 2-fluorophenylalanine, 3-fluorophenylalanine, 4-fluorophenylalanine, norleucine, cysteine, S-methylcysteine, 1,2,3,4-tetrahydroisoquinoline-3-carboxylic acid, homophenylalanine, DOPA, O-dimethyl-DOPA, 2-amino-4-(2-thienyl)butyric acid, benzodioxol-5-ylalanine, N-methyl-histidine, 2-amino-4-(3-thienyl)butyric acid, 3-(2-thienyl)serine, (Z)-dehydrophenylalanine, (E)-dehydrophenylalanine, 1,3-dioxolan-2-ylalanine, N-pyrrolylalanine, and 1-, 3- or 4-pyrazolylalanine;

$R^1$ is hydrogen, $(C_1-C_{10})$-alkyl, $(C_4-C_7)$-cycloalkyl, $(C_4-C_7)$-cycloalkyl-$(C_1-C_4)$-alkyl, $(C_6-C_{14})$-aryl, $(C_6-C_{14})$-aryl-$(C_1-C_4)$-alkyl or 1,3-dithiolar-2-yl-$(C_1-C_4)$-alkyl;

$R^2$ is hydrogen;

$R^3$ is a radical of the formula III:

in which $R^6$ is pyridyl; and q and s is each, independently of one another, 0, 1 or 2; and $R^9$ is hydrogen.

6. A method of inhibiting renin according to claim 5, wherein in said compound of the formula I:
said amino acid of the radical B is selected from the group consisting of phenylalanine, histidine, tyrosine, β-2-thienylalanine, β-3-thienylalanine, valine, methyltyrosine, norvaline, β-2-benzo[b]thienylalanine and β-3-benzo[b]-thienylalanine; and $R^1$ is $(C_4-C_7)$-cycloalkyl-$(C_1-C_4)$-alkyl.

7. A method of inhibiting renin according to claim 5, wherein the amount of the compound is effective to treat high blood pressure.

* * * * *

UNITED STATES PATENT AND TRADEMARK OFFICE
CERTIFICATE OF CORRECTION

PATENT NO. : 5,204,357
DATED : April 20, 1993
INVENTOR(S) : Rainer Henning et al.

It is certified that error appears in the above-indentified patent and that said Letters Patent is hereby corrected as shown below:

Claim 1, column 16, line 64, Formula IV, change "$R^7-S(O)_t-$" to --$R^7-S(O)_t-$--.

Claim 3, column 18, line 44, Formula IV, change "$R^7-S(O)_t-$" to --$R^7-S(O)_t-$--.

Claim 5, column 20, line 25, Formula IV, change "$R^7-S(O)_t-$" to --$R^7-S(O)_t-$--.

Claim 1, column 17, line 54, change "O-tertbutyltyrosine" to --O-tert.-butyltyrosine--.

Claim 3, column 19, line 36, change "O-tertbutyltyrosine" to --O-tert.-butyltyrosine--.

UNITED STATES PATENT AND TRADEMARK OFFICE
CERTIFICATE OF CORRECTION

PATENT NO. : 5,204,357
DATED : April 20, 1993
INVENTOR(S) : Rainer Henning et al.

It is certified that error appears in the above-indentified patent and that said Letters Patent is hereby corrected as shown below:

Claim 5, column 21, line 18, change "O-tertbutyltyrosine" to --O-tert.-butyltyrosine--.

Claim 2, column 18, line 20, change "B-3-benzo[b]-thienylalanine" to --B-3-benzo[b]thienylalanine--.

Claim 4, column 20, line 2, change "B-3-benzo[b]-thienylalanine" to --B-3-benzo[b]thienylalanine--.

Claim 6, column 22, line 23, change "B-3-benzo[b]-thienylalanine" to --B-3-benzo[b]thienylalanine--.

UNITED STATES PATENT AND TRADEMARK OFFICE
CERTIFICATE OF CORRECTION

PATENT NO.  : 5,204,357
DATED       : April 20, 1993
INVENTOR(S) : Rainer Henning et al.

It is certified that error appears in the above-indentified patent and that said Letters Patent is hereby corrected as shown below:

Claim 5, column 22, line 5, change "1,3-dithiolar-2-yl-" to --1,3-dithiolan-2-yl- --.

Signed and Sealed this

Eighteenth Day of October, 1994

Attest:

BRUCE LEHMAN

*Attesting Officer*    *Commissioner of Patents and Trademarks*